US012746405B2

(12) United States Patent
Carlson

(10) Patent No.: US 12,746,405 B2
(45) Date of Patent: Sep. 29, 2026

(54) REDUCING ELECTROSENSATION WHILST TREATING A SUBJECT USING ALTERNATING ELECTRIC FIELDS

(71) Applicant: Novocure GmbH, Root (CH)

(72) Inventor: Kristen W. Carlson, Concord, MA (US)

(73) Assignee: Novocure GmbH, Baar (CH)

( * ) Notice: Subject to any disclaimer, the term of this patent is extended or adjusted under 35 U.S.C. 154(b) by 770 days.

(21) Appl. No.: 17/955,656

(22) Filed: Sep. 29, 2022

(65) Prior Publication Data

US 2023/0098801 A1 Mar. 30, 2023

Related U.S. Application Data

(60) Provisional application No. 63/250,675, filed on Sep. 30, 2021.

(51) Int. Cl.
*A61N 1/40* (2006.01)

(52) U.S. Cl.
CPC .................................... *A61N 1/40* (2013.01)

(58) Field of Classification Search
CPC ........................................................ A61N 1/40
See application file for complete search history.

(56) References Cited

U.S. PATENT DOCUMENTS 6,868,289 B2 3/2005 Palti
7,016,725 B2 3/2006 Palti
7,089,054 B2 8/2006 Palti
7,136,699 B2 11/2006 Palti
7,333,852 B2 2/2008 Palti
7,467,011 B2 12/2008 Palti
7,519,420 B2 4/2009 Palti
7,565,205 B2 7/2009 Palti
7,565,206 B2 7/2009 Palti
7,599,745 B2 10/2009 Palti
(Continued)

FOREIGN PATENT DOCUMENTS

CN 202844368 U 4/2013
CN 104415454 A 3/2015
WO 2000056395 A1 9/2000

OTHER PUBLICATIONS

Eggers et al., "Combining direct current and kilohertz frequency alternating current to mitigate onset activity during electrical nerve block," Journal of Neural Engineering, vol. 18, p. 046010, Mar. 2021.

(Continued)

*Primary Examiner* — William J Levicky
*Assistant Examiner* — Jessandra F Hough
(74) *Attorney, Agent, or Firm* — Potomac Law Group, PLLC

(57) ABSTRACT

When treating a subject using alternating electric fields (e.g., using TTFields to treat a tumor), some subjects experience an electrosensation effect when the alternating electric field switches direction. This application describes a variety of approaches for reducing or eliminating this electrosensation. More specifically, during the course of treatment using alternating electric fields, additional electrical signals that reduce the subject's sensation are applied during each of a plurality of time intervals, and these additional electrical signals interact with the relevant nerve cells to reduce the sensations.

18 Claims, 6 Drawing Sheets

(56) References Cited

U.S. PATENT DOCUMENTS 7,599,746 B2 10/2009 Palti
7,706,890 B2 4/2010 Palti
7,715,921 B2 5/2010 Palti
7,805,201 B2 9/2010 Palti
7,890,183 B2 2/2011 Palti et al.
7,912,540 B2 3/2011 Palti
7,917,227 B2 3/2011 Palti
8,019,414 B2 9/2011 Palti
8,027,738 B2 9/2011 Palti
8,170,684 B2 5/2012 Palti
8,175,698 B2 5/2012 Palti et al.
8,229,555 B2 7/2012 Palti
RE43,618 E 8/2012 Palti
8,244,345 B2 8/2012 Palti
8,406,870 B2 3/2013 Palti
8,447,395 B2 5/2013 Palti et al.
8,447,396 B2 5/2013 Palti et al.
8,465,533 B2 6/2013 Palti
8,706,261 B2 4/2014 Palti
8,715,203 B2 5/2014 Palti
8,718,756 B2 5/2014 Paiti
8,764,675 B2 7/2014 Palti
9,023,090 B2 5/2015 Palti
9,023,091 B2 5/2015 Palti
9,039,674 B2 5/2015 Palti et al.
9,056,203 B2 6/2015 Palti et al.
9,440,068 B2 9/2016 Palti et al.
9,655,669 B2 5/2017 Palti et al.
9,750,934 B2 9/2017 Palti et al.
9,910,453 B2 3/2018 Wasserman et al.
10,188,851 B2 1/2019 Wenger et al.
10,441,776 B2 10/2019 Kirson et al.
10,779,875 B2 9/2020 Palti et al.
10,967,167 B2 4/2021 Hagemann et al.
11,191,956 B2 12/2021 Giladi et al.
2004/0176804 A1 9/2004 Palti
2005/0209642 A1* 9/2005 Palti ...................... A61N 1/326 607/2
2006/0167499 A1 7/2006 Palti
2006/0276858 A1 12/2006 Palti
2007/0225766 A1 9/2007 Palti
2007/0239213 A1 10/2007 Palti
2009/0076366 A1 3/2009 Palti
2011/0184486 A1* 7/2011 De Ridder ......... A61N 1/37264 607/45
2012/0029419 A1 2/2012 Palti
2012/0283726 A1 11/2012 Palti
2014/0330268 A1 11/2014 Palti et al.
2017/0120041 A1 5/2017 Wenger et al.
2017/0215939 A1 8/2017 Palti et al.
2017/0281934 A1 10/2017 Giladi et al.
2018/0001075 A1 1/2018 Kirson et al.
2018/0008708 A1 1/2018 Giladi et al.
2018/0050200 A1 2/2018 Wasserman et al.
2018/0160933 A1 6/2018 Urman et al.
2018/0202991 A1 7/2018 Giladi et al.
2018/0280687 A1 10/2018 Carter et al.
2019/0117956 A1 4/2019 Wenger et al.
2019/0117963 A1 4/2019 Travers et al.
2019/0224474 A1 7/2019 Yang et al.
2019/0308016 A1 10/2019 Wenger et al.
2020/0001069 A1 1/2020 Kirson et al.
2020/0009376 A1 1/2020 Chang et al.
2020/0009377 A1 1/2020 Chang et al.
2020/0016067 A1 1/2020 Gotlib et al.
2020/0023179 A1 1/2020 Bomzon et al.
2020/0061360 A1 2/2020 Hagemann et al.
2020/0061361 A1 2/2020 Hagemann et al.
2020/0069937 A1* 3/2020 Naveh .................. A61N 1/0476
2020/0078582 A1 3/2020 Alon et al.
2020/0108031 A1 4/2020 Borst et al.
2020/0114141 A1 4/2020 Bomzon et al.
2020/0114142 A1 4/2020 Bomzon et al.
2020/0121728 A1 4/2020 Wardak et al.
2020/0129761 A1 4/2020 Bomzon et al.
2020/0146586 A1 5/2020 Naveh et al.
2020/0155835 A1 5/2020 Wasserman et al.
2020/0171297 A1 6/2020 Kirson et al.
2020/0179512 A1 6/2020 Giladi et al.
2020/0219261 A1 7/2020 Shamir et al.
2020/0269037 A1 8/2020 Hagemann et al.
2020/0269041 A1 8/2020 Zeevi et al.
2020/0368525 A1 11/2020 Maag et al.
2021/0031031 A1 2/2021 Wasserman et al.
2021/0038584 A1 2/2021 Voloshin-Sela
2021/0060334 A1 3/2021 Avraham et al.
2021/0069503 A1 3/2021 Tran et al.
2021/0138233 A1 5/2021 Deslauriers
2021/0162228 A1 6/2021 Urman et al.
2021/0187277 A1 6/2021 Wasserman et al.
2021/0196348 A1 7/2021 Wasserman
2021/0199640 A1 7/2021 Patel et al.
2021/0203250 A1 7/2021 Wasserman
2021/0268247 A1 9/2021 Story et al.
2021/0299440 A1 9/2021 Deslauriers et al.
2021/0308446 A1 10/2021 Alon et al.
2021/0330950 A1 10/2021 Hagemann et al.
2021/0346694 A1 11/2021 Wasserman et al.
2021/0379362 A1 12/2021 Smith et al.
2021/0408383 A1 12/2021 Kalra et al.
2022/0088374 A1* 3/2022 Ackermann ............. A61N 1/40
2022/0095997 A1 3/2022 Wasserman
2022/0096821 A1 3/2022 Kirson et al.
2022/0118249 A1 4/2022 Bomzon et al.
2022/0161028 A1 5/2022 Giladi et al.
2022/0193435 A1 6/2022 Wasserman et al.
2022/0267445 A1 8/2022 Tran et al.
2022/0280787 A1 9/2022 Bomzon et al.
2022/0288395 A1 9/2022 Voloshin-Sela et al.
2022/0313992 A1 10/2022 Wasserman
2022/0323753 A1 10/2022 Voloshin-Sela et al.

OTHER PUBLICATIONS

Muzquiz et al., "A Reversible Low Frequency Alternating Current Nerve Conduction Block Applied to Mammalian Autonomic Nerves," Sensors, vol. 21, p. 4521, Jul. 2021.

Roldan et al., "Measurement of block thersholds in kiloHertz frequency alternating current peripheral nerve block," J. Neurosci. Methods, vol. 315, pp. 48-54, Mar. 2019.

Zupanic et al., "Increasing the repetition frequency of electric pulse delivery reduces unpleasant sensations that occur in electrochemotherapy," Neoplasma, vol. 54, No. 3, pp. 246-250, Jan. 2007.

International Search Report and Written Opinion issued in application PCT/IB2022/059265 dated Dec. 21, 2022.

* cited by examiner

REDUCING ELECTROSENSATION WHILST TREATING A SUBJECT USING ALTERNATING ELECTRIC FIELDS

BACKGROUND

Tumor Treating Fields (TTFields) therapy is a proven approach for treating tumors using alternating electric fields, e.g., at frequencies between 100-500 kHz (e.g., 150-200 kHz). FIG. 1 is a schematic representation of the prior art Optune® system for delivering TTFields. The TTFields are delivered to patients via four transducer arrays 21-24 that are placed on the patient's skin in close proximity to a tumor (e.g., as depicted in FIGS. 2A-2D for a person with glioblastoma). The transducer arrays 21-24 are arranged in two pairs, and each transducer array is connected via a multi-wire cable to an AC signal generator 20. The AC signal generator (a) sends an AC current through one pair of arrays 21, 22 during a first period of time, which induces an electric field with a first direction through the tumor; then (b) sends an AC current through the other pair of arrays 23, 24 during a second period of time, which induces an electric field with a second direction through the tumor; then repeats steps (a) and (b) for the duration of the treatment. Each transducer array 21-24 includes a plurality (e.g., between 9 and 20) capacitively coupled electrode elements, each of which has an electrically conductive substrate with a dielectric layer disposed thereon.

Alternating electric fields can also be used to treat medical conditions other than tumors. For example, as described in U.S. Pat. No. 10,967,167 (which is incorporated herein by reference in its entirety), alternating electric fields at frequencies between 75 kHz and 125 kHz can increase the permeability of the blood brain barrier (BBB) so that, e.g., chemotherapy drugs can reach the brain.

SUMMARY OF THE INVENTION

One aspect of the invention is directed to a first method of treating a target region of a subject's body with an alternating electric field. The first method comprises applying an alternating electric field to the target region during a course of treatment, wherein the alternating electric field has a frequency between 50 kHz and 500 kHz. The first method also comprises applying an electrical signal to the subject's body during each of a plurality of time intervals during the course of the treatment, wherein the electrical signal is configured to reduce the subject's sensation when the alternating electric field is applied during the course of the treatment.

In some instances of the first method, the alternating electric field has field lines that run through the subject's body between a first electrode element and a second electrode element, and the electrical signal travels through the subject's body in a direction that is substantially perpendicular to the field lines.

In some instances of the first method, the alternating electric field is applied by imposing an AC voltage between a first electrode element configured for positioning on or in the subject's body and a second electrode element configured for positioning on or in the subject's body. The first electrode element has a front face. The electrical signal is applied between a third electrode element configured for positioning on or in the subject's body and a fourth electrode element configured for positioning on or in the subject's body. The third electrode element has a front face having a centroid, and the fourth electrode element has a front face having a centroid. In these instances, a line between the centroid of the front face of the third electrode element and the centroid of the front face of the fourth electrode element is substantially parallel to the front face of the first electrode element.

In some instances of the first method, an orientation of the alternating electric field repeatedly alternates between at least two different directions during the course of treatment, and the electrical signal is applied to a plurality of different areas of the subject's body during the course of the treatment, and the application of the electrical signal to the different areas of the subject's body is synchronized with the alternation between the at least two different directions.

In some instances of the first method, the alternating electric field provides an anti-tumor effect. In some instances of the first method, the alternating electric field increases the permeability of the subject's blood-brain-barrier.

In some instances of the first method, the electrical signal during each of the plurality of time intervals increases an action potential threshold of nerve fibers. In some instances of the first method, the electrical signal during each of the plurality of time intervals blocks a propagation of an action potential of nerve fibers.

In some instances of the first method, the electrical signal during each of the plurality of time intervals comprises a train of at least 10 pulses. Optionally, in these instances, each of the pulses has a width of at least 100 μs. Optionally, in these instances, the train of pulses continues for at least 100 ms. Optionally, in these instances, the pulses are configured to provide a charge balanced waveform.

In some instances of the first method, the electrical signal during each of the plurality of time intervals has a frequency between 4 kHz and 30 kHz. In some instances of the first method, the electrical signal during each of the plurality of time intervals has a frequency between 1 and 2 Hz. In some instances of the first method, the electrical signal during each of the plurality of time intervals has a frequency between 0.1 and 30 Hz.

Optionally, in the instances described in the previous paragraph, the electrical signal during each of the plurality of time intervals has an amplitude of 0.5-10 mA. Optionally, in the instances described in the previous paragraph, the electrical signal during each of the plurality of time intervals is a DC signal having a duration between 1 and 60 s.

In some instances of the first method, the electrical signal during each of the plurality of time intervals is a DC signal having a duration of less than 10 s. In some instances of the first method, the electrical signal during each of the plurality of time intervals includes a plurality of different signals that are applied simultaneously. In some instances of the first method, the electrical signal during each of the plurality of time intervals includes a plurality of different signals that are applied sequentially. In some instances of the first method, the electrical signal during each of the plurality of time intervals includes a plurality of different signals that are applied sequentially, with gaps in time disposed therebetween.

In some instances of the first method, the electrical signal during each of the plurality of time intervals includes between 2 and 5 bursts of pulses, wherein each burst has a duration of 200-500 μs, wherein the bursts are generated at a rate of 10-60 Hz, and wherein the pulses within any given burst are generated at a rate of 200-400 Hz.

In some instances of the first method, the electrical signal during each of the plurality of time intervals comprises an anodic pulse having a first amplitude and a first duration and a cathodic pulse having a second amplitude and a second duration. The first duration is at least twice as long as the second duration, the first amplitude is less than half of the second amplitude, and the anodic pulse charge balances the cathodic pulse. Optionally, in these instances, the electrical signal during each of the plurality of time intervals further comprises an alternating current signal having a frequency between 1 and 30 kHz that continues a nerve fiber block with low probability of damage to nerve fibers. Optionally, in any of the instances described above in this paragraph, the cathodic pulse begins with a ramp-up in amplitude to eliminate a possible single nerve fiber action potential.

In some instances of the first method, the electrical signal during each of the plurality of time intervals is offset from zero amplitude. In some instances of the first method, each of the plurality of time intervals has a duration between 3 ms and 600 ms.

In some instances of the first method, no gaps in time exist between the plurality of time intervals. In some instances of the first method, a plurality of gaps in time are interposed between the plurality of time intervals. In some instances of the first method, gaps in time that are at least 15 seconds in duration are interposed between at least some of the plurality of time intervals.

In some instances of the first method, the alternating electric field is not applied to the target region during the plurality of time intervals.

In some instances of the first method, the electrical signal during at least some of the time intervals is below a threshold of nerve fibers that produces unwanted sensation. In some instances of the first method, the electrical signal during at least some of the time intervals is above a threshold of nerve fibers that produces unwanted sensation. In some instances of the first method, the electrical signal during at least some of the time intervals is below a threshold of 7-15 μm A-beta nerve fibers that produces sensations of at least one of vibration and paresthesia. In some instances of the first method, the electrical signal during at least some of the time intervals is above a threshold of 7-15 μm A-beta nerve fibers that produces sensations of at least one of vibration and paresthesia. In some instances of the first method, the electrical signal during each of the plurality of time intervals is below a threshold of nerve fibers that produces at least one of muscle twitching and contraction.

Another aspect of the invention is directed to a first apparatus for treating a target region of a subject's body with an alternating electric field. The first apparatus comprises an AC voltage generator having a first AC output that operates at a frequency between 50-500 kHz, and a signal generator configured to generate a first electrical signal during each of a plurality of first times during a course of treatment. The first electrical signal is configured to reduce the subject's sensation when a first alternating electric field is applied during the course of treatment. The first electrical signal can be configured to increase an action potential threshold of nerve fibers in the subject's body or to block propagation of an action potential of nerve fibers in the subject's body.

Some embodiments of the first apparatus further comprise a first electrode element configured for positioning on or in the subject's body and a second electrode element configured for positioning on or in the subject's body, and the first AC output is applied between the first electrode element and the second electrode element. These embodiments also further comprise a third electrode element configured for positioning on or in the subject's body and a fourth electrode element configured for positioning on or in the subject's body, and the first electrical signal is applied between the third electrode element and the fourth electrode element.

Optionally, in the embodiments described in the previous paragraph, the third electrode element is adjacent to and distinct from the first electrode element, and the fourth electrode element is adjacent to and distinct from the first electrode element. Optionally, in the embodiments described in the previous paragraph, the first electrode element and the second electrode element are capacitively-coupled electrode elements, and the third electrode element and the fourth electrode element are conductive electrode elements. Optionally, in the embodiments described in the previous paragraph, the first electrode element and the second electrode element are capacitively-coupled electrode elements, and the third electrode element and the fourth electrode element are conductive electrode elements made using a platinum-iridium alloy. Optionally, in the embodiments described in the previous paragraph, a single electrode element serves as both the first electrode element and the third electrode element.

In some embodiments of the first apparatus, the AC voltage generator has a second AC output that operates at a frequency between 50-500 kHz, and the AC voltage generator is configured to repeatedly alternate between (a) activating the first AC output and (b) activating the second AC output. In these embodiments, the signal generator is further configured to generate a second electrical signal during each of a plurality of second times during the course of the treatment, and the second electrical signal is configured to reduce the subject's sensation when a second alternating electric field is applied during the course of the treatment.

Optionally, the embodiments described in the previous paragraph may further comprise (1) a first electrode element configured for positioning on or in the subject's body and a second electrode element configured for positioning on or in the subject's body, wherein the first AC output is applied between the first electrode element and the second electrode element; (2) a third electrode element configured for positioning on or in the subject's body and a fourth electrode element configured for positioning on or in the subject's body, wherein the first electrical signal is applied between the third electrode element and the fourth electrode element; (3) a fifth electrode element configured for positioning on or in the subject's body and a sixth electrode element configured for positioning on or in the subject's body, wherein the second AC output is applied between the fifth electrode element and the sixth electrode element; and (4) a seventh electrode element configured for positioning on or in the subject's body and an eighth electrode element configured for positioning on or in the subject's body, wherein the second electrical signal is applied between the seventh electrode element and the eighth electrode element.

Optionally, in the embodiments described in the previous paragraph, the third electrode element is adjacent to and distinct from the first electrode element, and the fourth electrode element is adjacent to and distinct from the first electrode element. And the seventh electrode element is adjacent to and distinct from the fifth electrode element, and the eighth electrode element is adjacent to and distinct from the fifth electrode element. Optionally, in the embodiments described in the previous paragraph, the first electrode element, the second electrode element, the fifth electrode element, and the sixth electrode element are capacitively-coupled electrode elements, and the third electrode element, the fourth electrode element, the seventh electrode element, and the eighth electrode element are conductive electrode elements. Optionally, in the embodiments described in the previous paragraph, a single electrode element serves as both the first electrode element and the third electrode element, and another single electrode element serves as both the fifth electrode element and the seventh electrode element.

In some embodiments of the first apparatus, the first electrical signal during each first time comprises a train of at least 10 pulses. Optionally, in these embodiments, each of the pulses has a width of at least 100 μs. Optionally, in these embodiments, the train of pulses continues for at least 100 ms. Optionally, in these embodiments, the pulses are configured to provide a charge balanced waveform.

In some embodiments of the first apparatus, the first electrical signal during each first time has a frequency between 4 kHz and 30 kHz. In some embodiments of the first apparatus, the first electrical signal during each first time has a frequency between 1 and 2 Hz. In some embodiments of the first apparatus, the first electrical signal during each first time has a frequency between 0.1 and 30 Hz.

Optionally, in the embodiments described in the previous paragraph, the first electrical signal during each first time has an amplitude of 0.5-10 mA. Optionally, in the embodiments described in the previous paragraph, the first electrical signal during each first time is a DC signal having a duration between 1 and 60 s. In some embodiments of the first apparatus, the first electrical signal during each first time is a DC signal having a duration of less than 10 s.

In some embodiments of the first apparatus, the first electrical signal during each first time comprises an anodic pulse having a first amplitude and a first duration and a cathodic pulse having a second amplitude and a second duration. The first duration is at least twice as long as the second duration, the first amplitude is less than half of the second amplitude, and the anodic pulse charge balances the cathodic pulse. Optionally, in these embodiments, the first electrical signal during each first time further comprises an alternating current signal having a frequency between 1 and 30 kHz that continues a nerve fiber block with low probability of damage to nerve fibers. Optionally, in any of the embodiments described above in this paragraph, the cathodic pulse can begin with a ramp-up in amplitude to eliminate a possible single nerve fiber action potential.

In some embodiments of the first apparatus, the first electrical signal during each first time is offset from zero amplitude. In some embodiments of the first apparatus, each first time has a duration between 3 ms and 600 ms.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
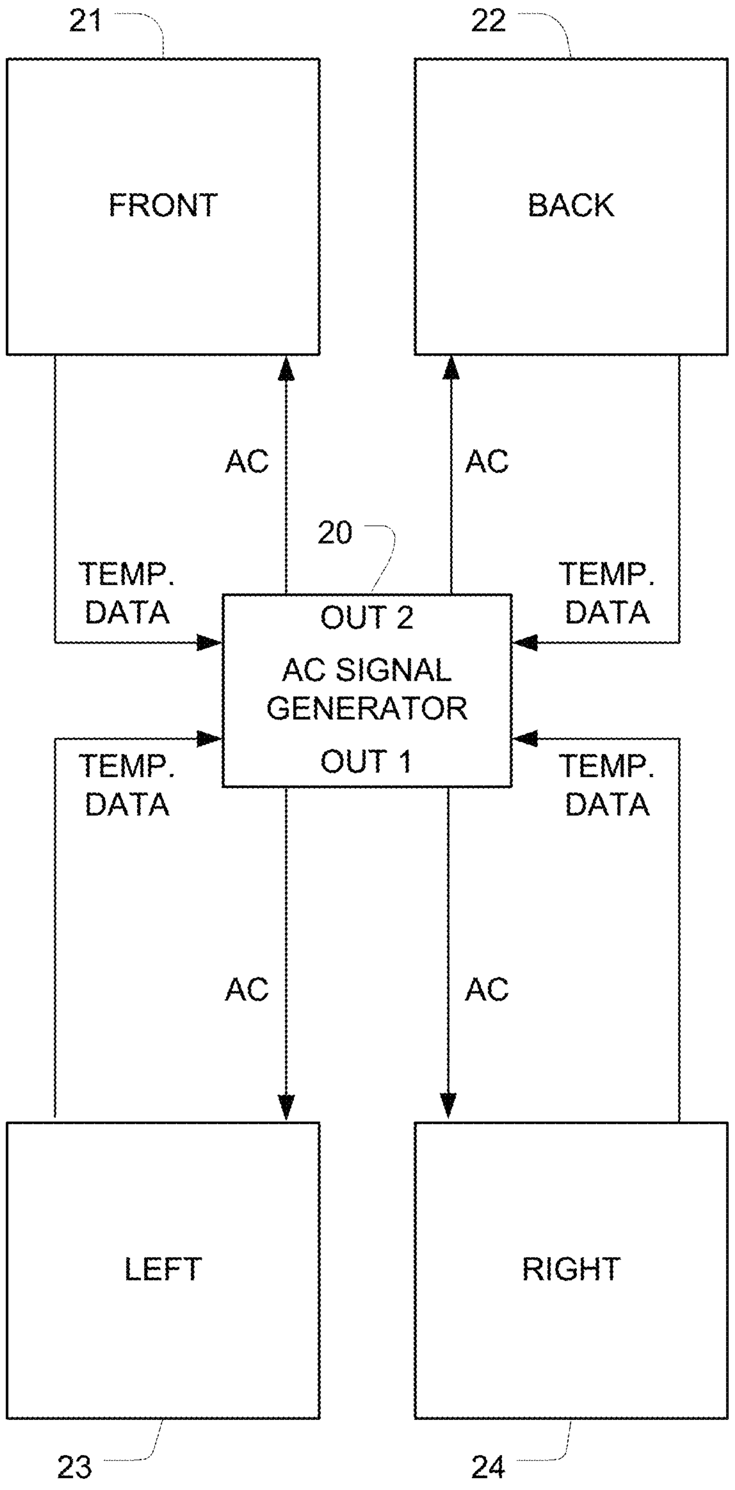
PRIOR ART FIG. 1
FIG. 1 is a schematic representation of the prior art Optune® system for delivering TTFields.
Figure 2A:
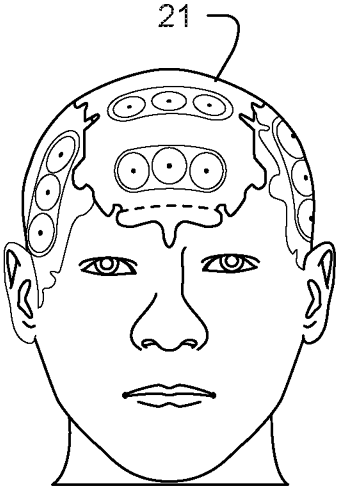
FIGS. 2A-2D depicts how four TTFields transducer arrays can be positioned on a subject's head for treating glioblastoma.
Figure 2B:
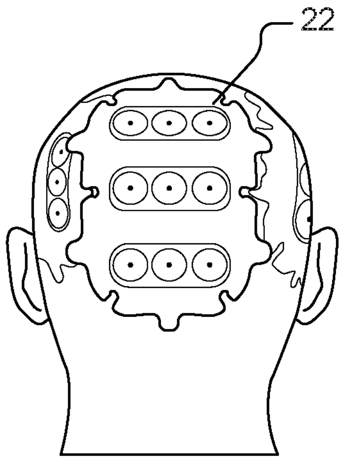
Figure 2C:
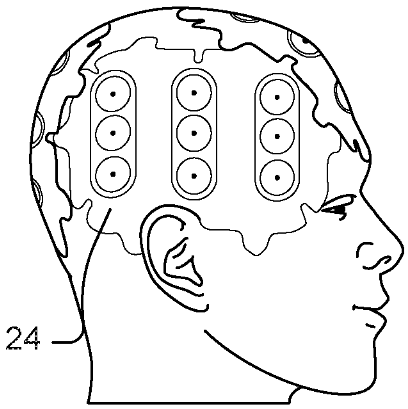
Figure 2D:
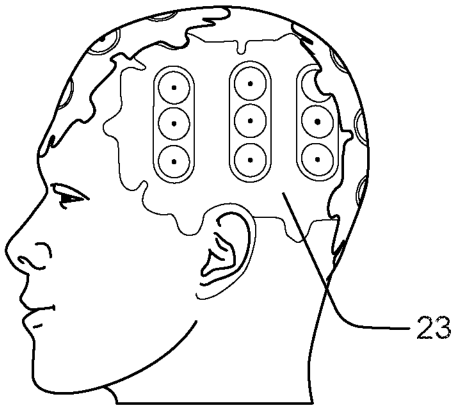

When treating a subject using alternating electric fields, higher amplitudes are strongly associated with higher efficacy of treatment. However, as the amplitude of the alternating electric field increases, and/or as the frequency of the alternating electric field decreases (e.g., to the vicinity of 100 kHz), some subjects experience an electrosensation effect when the alternating electric field switches direction. This electrosensation could be, for example, a vibratory sensation, paresthesia, and/or a twitching or contraction sensation of muscle fibers. And these sensations may discourage some subjects from continuing their treatment using alternating electric fields.

This application describes a variety of approaches for reducing or eliminating electrosensation while a subject is being treated with alternating electric fields. More specifically, during the course of treatment using alternating electric fields, additional electrical signals that reduce the subject's sensation are applied during each of a plurality of time intervals. The additional electrical signals are configured to reduce the subject's sensation when the alternating electric field is applied during the course of the treatment.

The electrosensation is believed to originate from interactions between the alternating electric fields and nerve cells (i.e., neurons) that are positioned near or adjacent to the transducer arrays. Without being bound by this theory, the additional electrical signal is believed to reduce the subject's sensation by increasing the action potential threshold of the relevant nerve cells and/or blocking a propagation of an action potential of nerve fibers.

I. Electrical Signals that can Ameliorate Electrosensation

One approach for reducing the subject's sensation is to apply an electrical signal that comprises a train of at least 10 pulses during each of the plurality of time intervals. In some embodiments such electrical signal may comprise a train of at least 12 pulses, at least 15 pulses, or at least 20 pulses. In some embodiments such electrical signal may comprise a train of 10 to 15 pulses or a train of 10 to 20 pulses. In some preferred embodiments, each of these pulses has a width of at least 100 μs. In some embodiments each of these pulses has a width of at least 150 μs, 200 μs, 250 μs, 300 μs, or 400 μs. In some embodiments each of these pulses has a width of 100 μs to 500 μs, 100 μs to 250 μs, or 100 μs to 200 μs. In some preferred embodiments, the train of pulses continues for at least 100 ms. In some embodiments, the train of pulses continues for at least 150 ms, 200 ms, 250 ms, 300 ms, or 400 ms. In some embodiments, the train of pulses continues for 100 ms to 500 ms, 100 to 250 ms, or 100 to 200 ms.

In some preferred embodiments, the pulses are configured to provide a charge balanced waveform. In some preferred embodiments, the electrical signal during each of the plurality of time intervals has a frequency between 4 kHz and 30 kHz, for example between 4 kHz and 20 kHz, 4 kHz and 10 kHz, 10 kHz and 20 kHz, 10 kHz and 30 kHz, or 20 kHz and 30 kHz. In some preferred embodiments, the electrical signal during each of the plurality of time intervals has a frequency between 1 and 2 Hz. In some embodiments, the electrical signal during each of the plurality of time intervals has a frequency between 0.1 and 30 Hz (e.g., 0.1-1 Hz, 1-10 Hz, 10-20 Hz, or 20-30 Hz). In some embodiments, the electrical signal during each of the plurality of time intervals has an amplitude of 0.5-10 mA. In some embodiments, the amplitude is 0.5 to 1 mA, 1 to 2 mA, or 2 to 10 mA. In some embodiments, the electrical signal during each of the plurality of time intervals has a duration between 1 and 60 s. In some embodiments, the electrical signal during each of the plurality of time intervals has a duration of less than 10 s (e.g., between 1 and 10 s, between 1 and 2 s, between 2 and 5 s, or between 5 and 10 s).

In some embodiments, the electrical signal during each of the plurality of time intervals includes a plurality of different signals that are applied simultaneously. In some embodiments, the electrical signal during each of the plurality of time intervals includes a plurality of different signals that are applied sequentially. In some embodiments, the electrical signal during each of the plurality of time intervals includes a plurality of different signals that are applied sequentially, with gaps in time disposed therebetween. In some embodiments, the electrical signal during each of the plurality of time intervals includes between 2 and 5 bursts of pulses, wherein each burst has a duration of 200-500 μs, wherein the bursts are generated at a rate of 10-60 Hz, and wherein the pulses within any given burst are generated at a rate of 200-400 Hz.

In some embodiments, the electrical signal during each of the plurality of time intervals comprises an anodic pulse having a first amplitude and a first duration and a cathodic pulse having a second amplitude and a second duration. The first duration is at least twice as long as the second duration, the first amplitude is less than half of the second amplitude, and the anodic pulse charge balances the cathodic pulse. Optionally, in these embodiments, the electrical signal during each of the plurality of time intervals further comprises an alternating current signal having a frequency between 1 and 30 kHz (e.g., between 1 and 5 kHz, or between 5 and 30 kHz) or between 0.1 and 30 Hz (e.g., 0.1-1 Hz, 1-10 Hz, 10-20 Hz, or 20-30 Hz) that continues a nerve fiber block with low probability of damage to nerve fibers. Optionally, in any of the embodiments described in this paragraph, the cathodic pulse begins with a ramp-up in amplitude to eliminate a possible single nerve fiber action potential.

In some preferred embodiments, the electrical signal during each of the plurality of time intervals is offset from zero amplitude. In some embodiments, each of the plurality of time intervals has a duration between 1 ms and 1000 ms, between 1 ms and 750 ms, between 1 ms and 500 ms, between 1 ms and 10 ms, between 10 ms and 50 ms, between 100 ms and 250 ms, or between 500 and 750 ms. In some preferred embodiments, each of the plurality of time intervals has a duration between 3 ms and 600 ms.

Another approach for reducing the subject's sensation is to apply an electrical signal having a frequency between 0.25 and 10 Hz (e.g., between 0.5 and 5 Hz, or between 1 and 2 Hz) during each of the plurality of time intervals. In these embodiments, the electrical signal during each of the plurality of time intervals may optionally be offset from zero amplitude. In these embodiments, each of the plurality of time intervals may have a duration between 100 ms and 30 s, between 200 ms and 20 s, between 500 ms and 20 s, or between 500 ms and 10 s.

The electrical signals that are applied during at least some of the time intervals may be below a threshold of nerve fibers that produces unwanted sensation, or may be above that threshold. In some embodiments, the electrical signals are initially applied below the threshold of nerve fibers that produce unwanted sensation, and after the initial electrical signals have caused an increase in the action potential threshold of the relevant nerve cells, their amplitude is subsequently increased to above that threshold. The electrical signals that are applied during at least some of the time intervals may be below a threshold of 7-15 μm A-beta nerve fibers that produces sensations of at least one of vibration and paresthesia, or may be above that threshold. In some embodiments, the electrical signals are initially applied below the threshold of 7-15 μm A-beta nerve fibers that produces sensations of at least one of vibration and paresthesia, and after the initial electrical signals have caused an increase in the action potential threshold of the relevant nerve cells, their amplitude is subsequently increased to above that threshold. Preferably, the electrical signal during each of the plurality of time intervals is always below a threshold of nerve fibers that produces at least one of muscle twitching and contraction.

II. Embodiments that Use the Electrosensation-Ameliorating Signals

Figure 3:
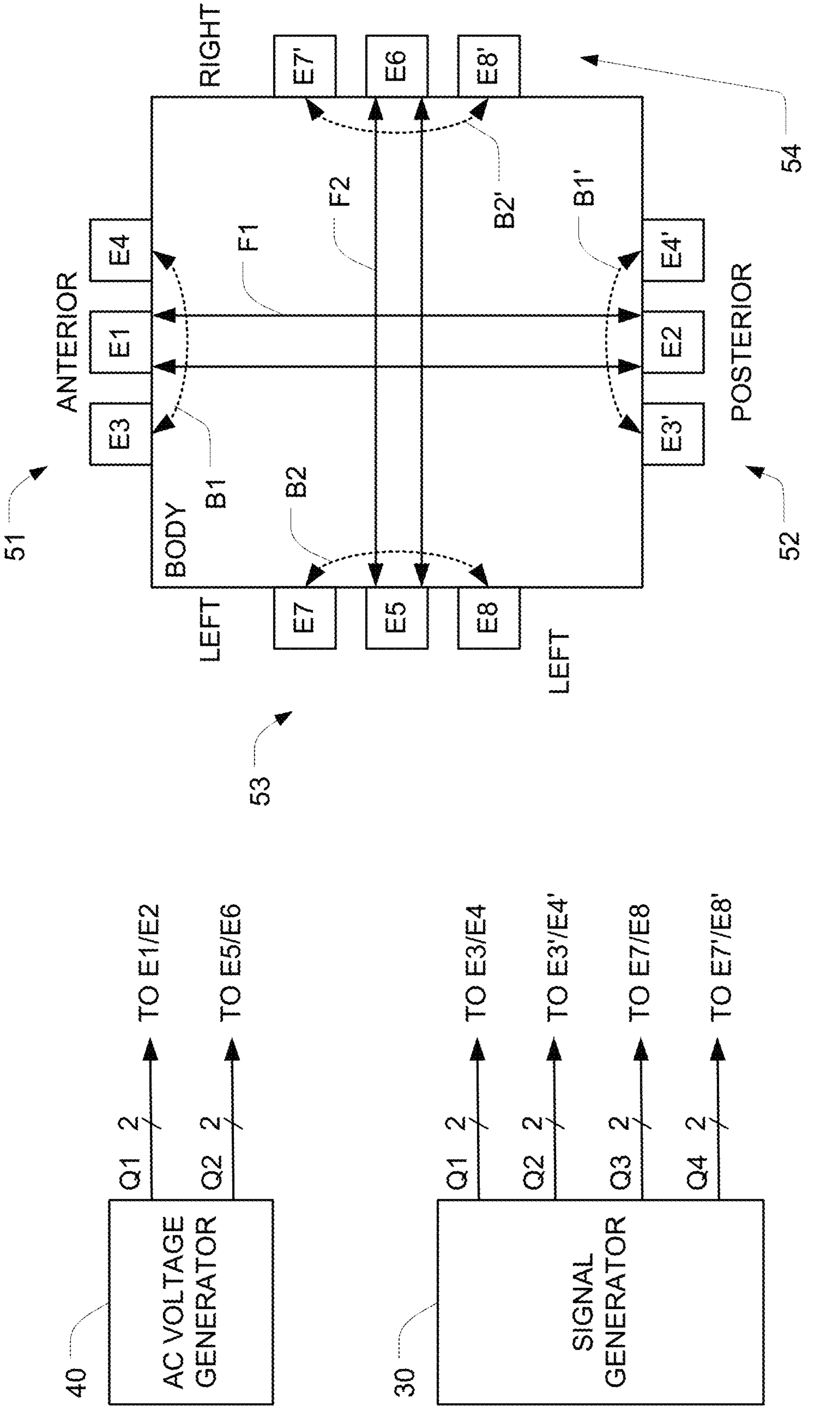
FIG. 3 depicts an apparatus for treating a target region of a subject's body with an alternating electric field.

FIG. 3 depicts an apparatus for treating a target region of a subject's body with an alternating electric field. The FIG. 3 embodiment includes an AC voltage generator 40 that generates first and second AC outputs at a frequency between 50-500 kHz. In alternative embodiments, the frequency can be between 50 kHz and 1 MHz. The frequency of the AC voltage generator 40 will depend on the type of treatment. For example, to treat a tumor using TTFields, the frequency could be between 150 and 200 kHz. Alternatively, to increase the permeability of a subject's blood-brain barrier, the frequency could be between 50 kHz and 200 kHz, for example 100 kHz.

In the example depicted in FIG. 3, a first set of electrode elements 51 (which includes first electrode element E1) is positioned on the anterior side of the subject's body, and a second set of electrode elements 52 (which includes second electrode element E2) is positioned on the posterior side of the subject's body. When the first AC output of the AC voltage generator 40 is applied between electrode element E1 in the first set of electrode elements 51 and electrode element E2 in the second set of electrode elements 52, an alternating electric field is induced through the target region in direction F1 (i.e., the vertical direction in FIG. 3). The frequency of the alternating electric field will match the frequency of the AC voltage generator 40.

The first set of electrode elements 51 also includes third electrode element E3 and fourth electrode element E4. A signal generator 30 is configured to generate a first electrical signal during each of a plurality of first times during the course of treatment. The nature of the first electrical signal is as described above in section I. When the first electrical signal from the signal generator 30 is applied between the third electrode element E3 and the fourth electrode element E4, an electrical signal will travel between those electrode elements E3, E4, as indicated by the dotted line B1. The electrical signal that is generated by the signal generator 30 is configured to reduce the subject's sensation when the alternating electric field is applied during the course of the treatment (e.g., by using a pulse train with the characteristics described above). Notably, when the electrode elements are positioned on the skin of the subject's body, the electrical signal travels close to the surface of the subject's body. Because the electrode elements E3 and E4 in the FIG. 3 example are positioned adjacent to and on either side of the first electrode element E1, the electrical signal that travels between electrode elements E3 and E4 will traverse the area of skin beneath electrode element E1, and will therefore reduce electrosensation attributable to electrode element E1 during times that electrode element E1 is active. Note that, as used herein, adjacent means nearby; and a touching or abutting relationship is not required by the word adjacent.

Similarly, the second set of electrode elements 52 includes electrode element E3' and electrode element E4' positioned adjacent to and on either side of the second electrode element E2. When an electrical signal (e.g., as described above in section I) from the signal generator 30 is applied between the electrode element E3' and the electrode element E4', an electrical signal will travel between those electrode elements E3', E4', as indicated by the dotted line B1'. Similar to the electrical signal that travels between electrode elements E3 and E4 (which reduces electrosensation attributable to electrode element E1), the electrical signal that travels between electrode elements E3' and E4' will traverse the area of skin beneath electrode element E2, and will therefore reduce electrosensation attributable to electrode element E2 during times that electrode element E2 is active.

The alternating electric field has field lines that run through the subject's body between the first electrode element E1 and the second electrode element E2 in direction F1, and the electrical signal travels through the subject's body in a direction B1 that is substantially perpendicular to those field lines. As used herein, "substantially perpendicular" means within 100 of true perpendicular. Note that the path B1 of the electrical signal between electrode elements E3 and E4, which is depicted in FIG. 3 as a curved line, is not drawn to scale. In practice, the electrical signal between those two electrode elements will travel very close to the surface of the subject's body.

The alternating electric field is applied by imposing an AC voltage between the first electrode element E1 (which is configured for positioning on or in a subject's body) and the second electrode element E2 (which is also configured for positioning on or in the subject's body). The front face of the first electrode element E1 is the face that faces the subject's body. The electrical signal (e.g., as described above in section I) is applied between the third electrode element E3 (which is configured for positioning on or in the subject's body) and the fourth electrode element E4 (which is also configured for positioning on or in the subject's body). The third and fourth electrode elements each has a front face having a centroid. The geometric relationship between the first, third, and fourth electrode elements E1, E3, E4 is such that a line between the centroid of the front face of the third electrode element E3 and the centroid of the front face of the fourth electrode element E4 will be substantially parallel to the front face of the first electrode element E1. As used herein, "substantially parallel" means within 10° of true parallel.

A third set of electrode elements 53 (which includes fifth electrode element E5) is positioned on the left side of the subject's body, and a fourth set of electrode elements 54 (which includes sixth electrode element E6) is positioned on the right side of the subject's body. When a second AC output of the AC voltage generator 40 is applied between electrode element E5 in the third set of electrode elements 53 and electrode element E6 in the fourth set of electrode elements 54, an alternating electric field is induced through the target region in direction F2 (i.e., the horizontal direction in FIG. 3). The frequency of the alternating electric field will match the frequency of the AC voltage generator 40.

The third set of electrode elements 53 also includes seventh electrode element E7 and eighth electrode element E8. The signal generator 30 is configured to generate a second electrical signal (e.g., as described above in section I) during each of a plurality of second times during the course of treatment. When the second electrical signal from the signal generator 30 is applied between the seventh electrode element E7 and the eighth electrode element E8, an electrical signal will travel between those electrode elements E7, E8, as indicated by the dotted line B2. Electrode elements E7 and E8 in the FIG. 3 example are positioned adjacent to and on either side of the fifth electrode element E5. Similar to the electrical signal that travels between electrode elements E3 and E4 (which reduces electrosensation attributable to electrode element E1), the electrical signal that travels between electrode elements E7 and E8 will traverse the area of skin beneath electrode element E5, and will therefore reduce electrosensation attributable to electrode element E5 during times that electrode element E5 is active.

Similarly, the fourth set of electrode elements 54 includes electrode element E7' and electrode element E8' positioned adjacent to and on either side of the sixth electrode element E6. When an electrical signal (e.g., as described above in section I) from the signal generator 30 is applied between the electrode element E7' and the electrode element E8', an electrical signal will travel between those electrode elements E7', E8', as indicated by the dotted line B2'. Similar to the electrical signal that travels between electrode elements E3 and E4 (which reduces electrosensation attributable to electrode element E1), the electrical signal that travels between electrode elements E7' and E8' will traverse the area of skin beneath electrode element E6, and will therefore reduce electrosensation attributable to electrode element E6 during times that electrode element E6 is active.

Notably, because certain electrode elements are only used for applying the alternating electric fields, and other electrode elements are only used for applying the electrical signal, the characteristics of each electrode element can be optimized for the particular purpose that it will be used. For example, the first, second, fifth, and sixth electrode elements E1, E2, E5, E6 can be capacitively-coupled electrode elements while the third, fourth, seventh, and eighth electrode elements E3, E4, E7, E8 can be conductive electrode elements (e.g., made using a platinum-iridium alloy). But in alternative embodiments, the first, second, fifth, and sixth electrode elements E1, E2, E5, E6 could be conductive electrode elements. Or the third, fourth, seventh, and eighth electrode elements E3, E4, E7, E8 could be capacitively-coupled electrode elements.

The AC voltage generator 40 may be configured to repeatedly alternate between (a) activating the first AC output and (b) activating the second AC output. The AC voltage generator 40 may switch between these two states every 1 second, or at a different interval (e.g., between 50 ms and 10 s). Whenever the first output of the AC voltage generator 40 is active, AC is applied between electrode element E1 in the first set of electrode elements 51 and electrode element E2 in the second set of electrode elements 52, and an alternating electric field is induced through the target region in direction F1 (i.e., the vertical direction in FIG. 3). Whenever the second AC output of the AC voltage generator 40 is active, AC is applied between electrode element E5 in the third set of electrode elements 53 and electrode element E6 in the fourth set of electrode elements 54, an alternating electric field is induced through the target region in direction F2 (i.e., the horizontal direction in FIG. 3). The orientation of the alternating electric field will therefore repeatedly alternate back and forth between direction F1 and direction F2.

The electrical signal from the signal generator 30 is applied to the subject's body during each of a plurality of time intervals during the course of the treatment. In some embodiments, the application of the electrical signal to the different areas of the subject's body is synchronized with the alternation of the alternating electric field between the different directions (e.g., as described below in connection with FIGS. 5-9).

In many anatomic locations, it is preferable to use an alternating electric field whose orientation alternates between different directions, as described above. But in other anatomic locations (e.g., in the spine), an alternating electric field with a constant orientation may be used. In these situations, only the first and second sets of electrode elements 51, 52 are necessary, and the third and fourth sets of electrode elements 53, 54 may be omitted. And the portions of the signal generator 30 and the AC voltage generator 40 that drive the third and fourth sets of electrode elements 53, 54 may also be omitted.

In the example depicted in FIG. 3, the third and fourth electrode elements E3, E4 are adjacent to and distinct from the first electrode element E1, electrode elements E3', E4' are adjacent to and distinct from the second electrode element E2, the seventh and eighth electrode elements E7, E8 are adjacent to and distinct from the fifth electrode element E5, and electrode elements E7', E8' are adjacent to and distinct from the sixth electrode element E6. But in alternative embodiments, a single physical electrode element may serve as more than one of these electrode elements simultaneously, or a single physical electrode element may serve as more than one of these electrode elements at different times. An example of this situation is described below in connection with FIG. 4.

Figure 4:
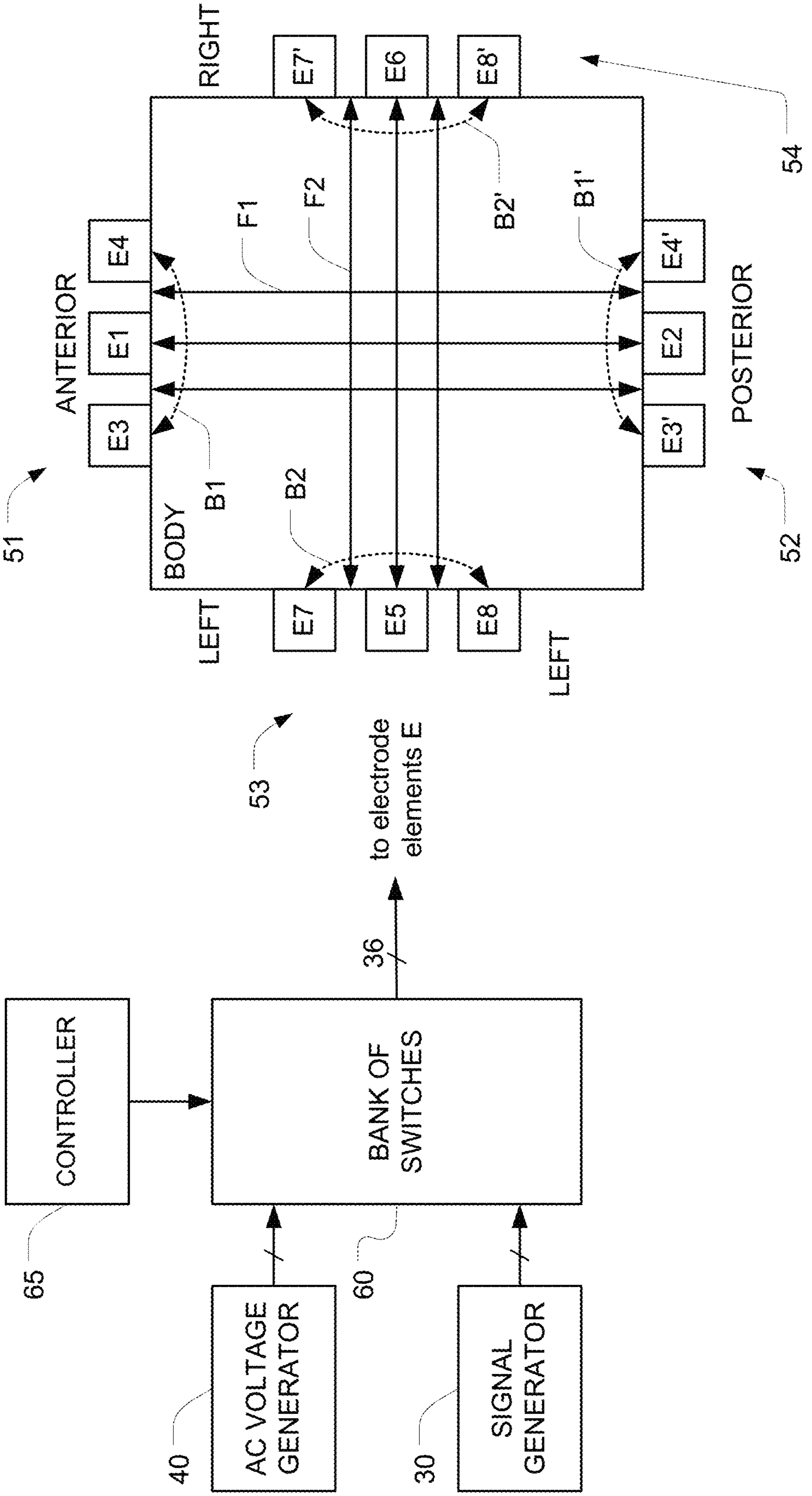
FIG. 4 depicts another apparatus for treating a target region of a subject's body with an alternating electric field.

FIG. 4 depicts another apparatus for treating a target region of a subject's body with an alternating electric field. A first set of electrode elements 51 is positioned on the anterior side of the subject's body, and a second set of electrode elements 52 is positioned on the posterior side of the subject's body. Third and fourth sets of electrode elements 53, 54 are positioned on the left and right side of the subject's body, respectively. Although FIG. 4 only shows three electrode elements in each of the sets of electrode elements 51-54, in practice, each of these sets of electrode elements 51-54 may include a larger number of electrode elements. For example, each of the sets of electrode elements 51-54 may include 9 electrode elements arranged in a 3×3 array configuration, similar to the configuration shown in FIG. 2A-2D. Alternatively, each of the sets of electrode elements 51-54 may include a different number (e.g., between 4 and 30) electrode elements.

The FIG. 4 embodiment includes an AC voltage generator 40 that generates first and second AC outputs at a frequency between 50-500 kHz. In alternative embodiments, the frequency can be between 50 kHz and 1 MHz. The frequency of the AC voltage generator 40 will depend on the type of treatment. For example, to treat a tumor using TTFields, the frequency could be between 150 and 200 kHz. Alternatively, to increase the permeability of a subject's blood-brain barrier, the frequency could be between 50 and 200 kHz, for example 100 kHz.

The FIG. 4 embodiment also includes a signal generator 30 configured to generate a first electrical signal (e.g., as described above in section I) during each of a plurality of first times during a course of treatment. The first electrical signal is configured to reduce the subject's sensation when a first alternating electric field is applied during the course of treatment (e.g., by using a pulse train with the characteristics described above). The signal generator 30 is also configured to generate a second electrical signal during each of a plurality of second times during a course of treatment. The second electrical signal is configured to reduce the subject's sensation when a second alternating electric field is applied during the course of treatment (e.g., by using a pulse train with the characteristics described above). Note that while FIG. 4 depicts the AC voltage generator 40 and the signal generator 30 as two distinct blocks, those two blocks may be combined into a single piece of hardware, particularly in those embodiments where the AC voltage is never applied simultaneously with the electrical signal (e.g., as described below in connection with FIGS. 7 and 9)

Notably, the FIG. 4 embodiment includes a bank of switches 60, which is configured to, in response to control signals received from a controller 65, route specific outputs of the AC voltage generator 40 or specific outputs of the signal generator 30 to specific electrode elements within each of the sets of electrode elements 51-54 as described below, in order to implement each of the functions described below (i.e., functions #1-4). The bank of switches 60 may be constructed, for example, using a bank of field effect transistors or solid-state relays.

Function #1—inducing a field in direction F1: The controller 65 sets up the switches in the bank 60 so that a first AC output of the AC voltage generator 40 is applied between all the electrode elements in the first set of electrode elements 51 and all the electrode elements in the second set of electrode elements 52. This will induce an alternating electric field through the target region in the body in direction F1 (i.e., the vertical direction in FIG. 4). The frequency of the alternating electric field will match the frequency of the AC voltage generator 40.

Function #2—inducing a field in direction F2: The controller 65 sets up the switches in the bank 60 so that a second AC output of the AC voltage generator 40 is applied between all the electrode elements in the third set of electrode elements 53 and all the electrode elements in the fourth set of electrode elements 54. This will induce an alternating electric field through the target region in direction F2 (i.e., the horizontal direction in FIG. 4). The frequency of the alternating electric field will match the frequency of the AC voltage generator 40.

The AC voltage generator 40 is configured to repeatedly alternate between (a) activating the first AC output and (b) activating the second AC output. The AC voltage generator 40 may switch between these two states every 1 second, or at a different interval (e.g., between 50 ms and 10 s). During step (a), the bank of switches 60 routes the first output of the AC voltage generator 40 between all the electrode elements in the first set of electrode elements 51 and all the electrode elements in the second set of electrode elements 52, and an alternating electric field is induced through the target region in direction F1 (i.e., the vertical direction in FIG. 4). During step (b), the bank of switches routes the second AC output of the AC voltage generator 40 between all the electrode elements in the third set of electrode elements 53 and all the electrode elements in the fourth set of electrode elements 54, and an alternating electric field is induced through the target region in direction F2 (i.e., the horizontal direction in FIG. 4). The orientation of the alternating electric field will therefore repeatedly alternate back and forth between direction F1 and direction F2, which provides the desired therapeutic effect (e.g., treating a tumor or increasing the permeability of the BBB).

During step (a), the subject may experience electrosensation adjacent to the first and second sets of electrode elements 51, 52. And during step (b), the subject may experience electrosensation adjacent to the third and fourth sets of electrode elements 53, 54.

Function #3—reducing electrosensation at the first and second sets of electrode elements 51, 52: The electrosensation adjacent to the first set of electrode elements 51 can be ameliorated by applying an electrical signal (e.g., as described above in section I) between different electrode elements located within the first set of electrode elements. The electrical signal that is generated by the signal generator 30 is configured to reduce the subject's sensation when the alternating electric field is applied during the course of the treatment. Some characteristics of these electrical signals which make them more effective at ameliorating electrosensation (e.g., using a train of at least 10 pulses, using a pulse width of at least 100 μs, continuing the train of pulses for at least 100 ms, etc.) are discussed above. The timing of these electrical signals with respect to the applied alternating electric fields is discussed below in connection with FIGS. 5-9.

The first set of electrode elements 51 is the anterior set. Assume, for purposes of discussion, that the first set of electrode elements 51 is a 3×3 array of electrode elements. The signal generator 30 is configured to generate a first electrical signal (e.g., as described above in section I) during each of a plurality of first times (e.g., the times labeled B1 in FIGS. 5-9) during the course of treatment. In response to commands issued by the controller 65, the bank of switches 60 will route a first electrical signal between all of the electrode elements on the left side of the anterior array and all of the electrode elements on the right side of the anterior array. The electrical signal will then travel between those electrode elements (including, e.g., between elements E3 and E4) as indicated by the dotted line B1. This will reduce the electrosensation at the first set of electrode elements 51. The directionality of these electrical signals is substantially parallel to the front faces of the electrode elements within the first set of electrode elements 51.

Ameliorating electrosensation adjacent to the second set of electrode elements 52 is similar to the amelioration for the first set of electrode elements 51 described above. The second set of electrode elements 52 is the posterior set. Assume, for purposes of discussion, that the second set of electrode elements 51 is a 3×3 array of electrode elements. The signal generator 30 is configured to generate a first electrical signal (e.g., as described above in section I) during each of a plurality of first times (e.g., the times labeled B1 in FIGS. 5-9) during the course of treatment. In response to commands issued by the controller 65, the bank of switches 60 will route a first electrical signal between all of the electrode elements on the left side of the posterior array and all of the electrode elements on the right side of the posterior array. The electrical signal will then travel between those electrode elements (including, e.g., between elements E3' and E4') as indicated by the dotted line B1'. This will reduce the electrosensation at the second set of electrode elements 52. The directionality of these electrical signals is substantially parallel to the front faces of the electrode elements within the second set of electrode elements 52.

Function #4—reducing electrosensation at the third and fourth sets of electrode elements 53, 54: Ameliorating electrosensation adjacent to the third set of electrode elements 53 is similar to the amelioration for the first set of electrode elements 51 described above. The third set of electrode elements 53 is the left set. Assume, for purposes of discussion, that the third set of electrode elements 51 is a 3×3 array of electrode elements. The signal generator 30 is configured to generate a second electrical signal (e.g., as described above in section I) during each of a plurality of second times (e.g., the times labeled B2 in FIGS. 5-9) during the course of treatment. In response to commands issued by the controller 65, the bank of switches 60 will route a second electrical signal between all of the electrode elements on the anterior side of the left array and all of the electrode elements on the posterior side of the left array. The electrical signal will then travel between those electrode elements (including, e.g., between elements E7 and E8) as indicated by the dotted line B2. This will reduce the electrosensation at the third set of electrode elements 53. The directionality of these electrical signals is substantially parallel to the front faces of the electrode elements within the third set of electrode elements 53.

Ameliorating electrosensation adjacent to the fourth set of electrode elements 54 is similar to the amelioration for the first set of electrode elements 51 described above. The fourth set of electrode elements 54 is the right set. Assume, for purposes of discussion, that the fourth set of electrode elements 51 is a 3×3 array of electrode elements. The signal generator 30 is configured to generate a second electrical signal during each of a plurality of second times (e.g., the times labeled B2 in FIGS. 5-9) during the course of treatment. In response to commands issued by the controller 65, the bank of switches 60 will route a second electrical signal between all of the electrode elements on the anterior side of the right array and all of the electrode elements on the posterior side of the right array. The electrical signal will then travel between those electrode elements (including, e.g., between elements E7' and E8') as indicated by the dotted line B2'. This will reduce the electrosensation at the fourth set of electrode elements 54. The directionality of these electrical signals is substantially parallel to the front faces of the electrode elements within the fourth set of electrode elements 54.

Notably, in this FIG. 4 embodiment, at least some of the individual electrode elements within the first set of electrode elements 51 are used to apply alternating electric fields during certain times, and are also used to apply the electrical signal (e.g., as described above in section I) during other times (or simultaneously with the certain times). This is also true for at least some of the individual electrode elements within the second set of electrode elements 52, at least some of the individual electrode elements within the third set of electrode elements 53, and at least some of the individual electrode elements within the fourth set of electrode elements 54. But in a variation of this FIG. 4 embodiment, certain electrode elements can be dedicated for applying the alternating electric field only, while certain other electrode elements can be dedicated for applying the electrical signal only. In these embodiments, the characteristics of the electrode elements can be tailored to match the signal that will be applied. For example, an electrode element that is dedicated for applying alternating electric fields only may be constructed using a conductive pad covered by a thin dielectric layer, while an electrode element that is dedicated for applying the electrical signal only may be constructed using a conductive pad (e.g., made using a platinum-iridium alloy) without no dielectric layer.

Figure 5:
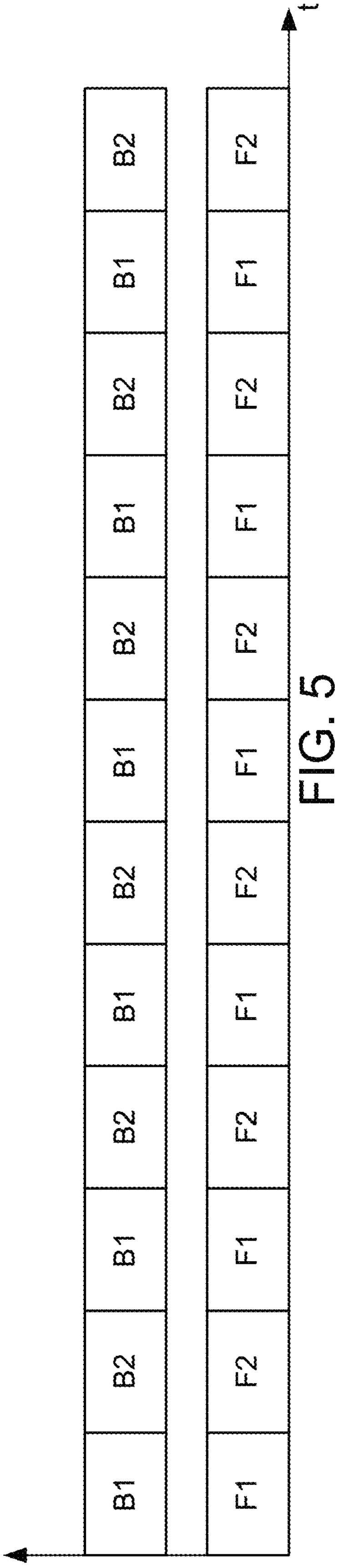
FIG. 5 depicts one example of a suitable timing relationship between the electrical signals and the alternating electric fields.

FIG. 5 depicts one example of a suitable timing relationship between the electrical signals (which reduce the subject's sensation, e.g., as described above in section I) and the alternating electric fields. As explained above in connection with FIGS. 3 and 4, the orientation of the alternating electric field repeatedly alternates back and forth between direction F1 and direction F2. In the FIG. 5 example, a first electrical signal B1 from the signal generator 30 is applied for the entire time that the alternating electric field is being applied in direction F1, and a second electrical signal B2 from the signal generator 30 is applied for the entire time that the alternating electric field is being applied in direction F2, and no gaps in time exist between any two adjacent electrical signals. The first electrical signal B1 will reduce the subject's sensation of the alternating electric field that is being applied in direction F1, and the second electrical signal B2 will reduce the subject's sensation of the alternating electric field that is being applied in direction F2. Notably, in this example, the electrical signals B1 are applied simultaneously with the alternating electric field in direction F1, and the electrical signals B2 are applied simultaneously with the alternating electric field in direction F2.

Figure 6:
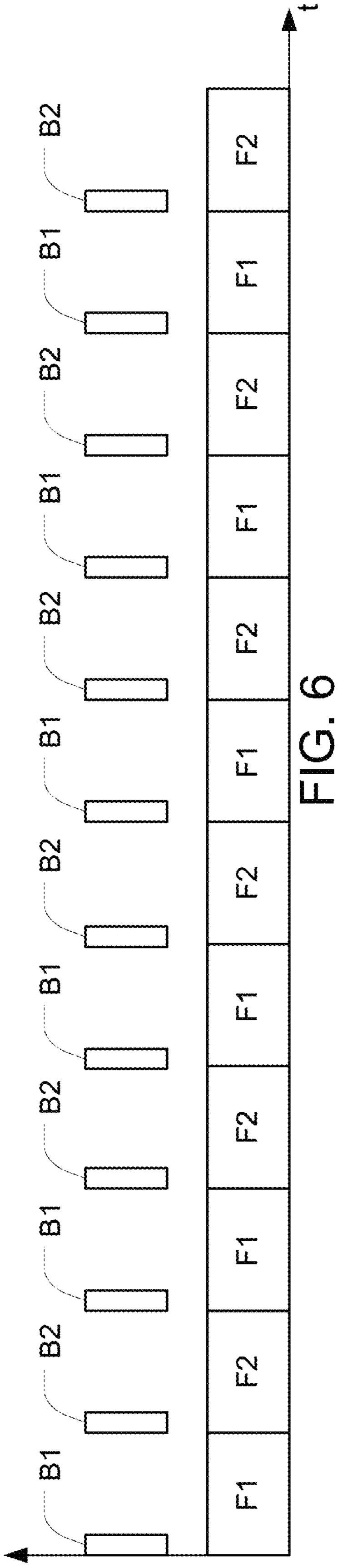
FIG. 6 depicts another example of a suitable timing relationship between the electrical signals and the alternating electric fields.

FIG. 6 depicts another example of a suitable timing relationship between the electrical signals (which reduce the subject's sensation, e.g., as described above in section I) and the alternating electric fields. As explained above in connection with FIGS. 3 and 4, the orientation of the alternating electric field repeatedly alternates back and forth between direction F1 and direction F2. The inventors have recognized that the electrosensation is much more pronounced during short periods of time immediately after the alternating electric field in a given direction is turned on. Accordingly, the electrical signals may be applied only during these short periods of time. In the FIG. 6 example, a first electrical signal B1 from the signal generator 30 is applied during the initial portion (e.g., the initial 100-300 ms) of each time that the alternating electric field is being applied in direction F1, and a second electrical signal B2 from the signal generator 30 is applied during the initial portion (e.g., the initial 100-300 ms) of each time that the alternating electric field is being applied in direction F2. Thus, in this example, gaps in time are interposed between any two adjacent electrical signals. The first electrical signal B1 will reduce the subject's sensation of the alternating electric field that is being applied in direction F1, and the second electrical signal B2 will reduce the subject's sensation of the alternating electric field that is being applied in direction F2. Notably, in this example, the electrical signals B1 are applied simultaneously with the onset of the alternating electric field in direction F1, and the electrical signals B2 are applied simultaneously with the onset of the alternating electric field in direction F2.

Figure 7:
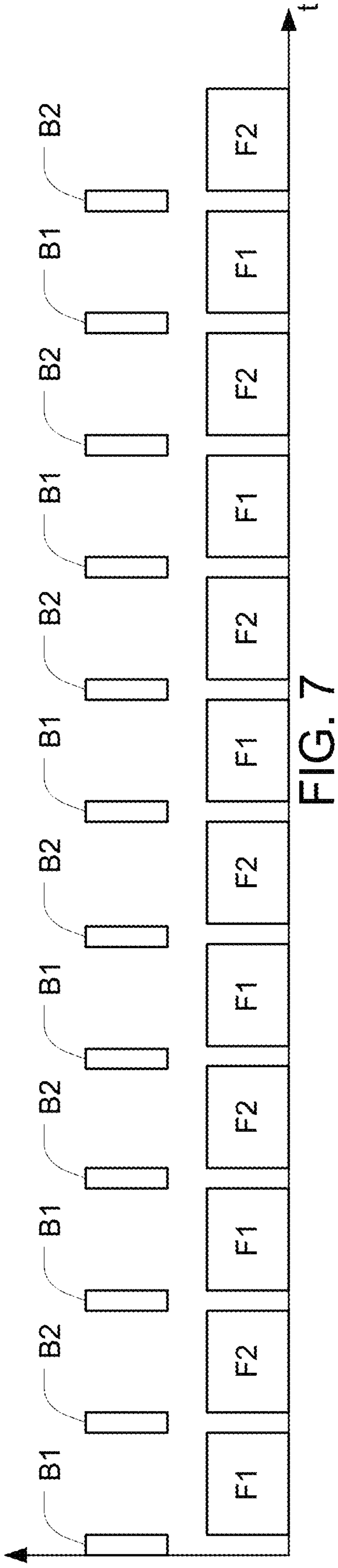
FIG. 7 depicts another example of a suitable timing relationship between the electrical signals and the alternating electric fields.

FIG. 7 depicts another example of a suitable timing relationship between the electrical signals (which reduce the subject's sensation, e.g., as described above in section I) and the alternating electric fields. As explained above in connection with FIGS. 3 and 4, the orientation of the alternating electric field repeatedly alternates back and forth between direction F1 and direction F2. As noted above, the electrosensation is much more pronounced during short periods of time immediately after the alternating electric field in a given direction is turned on. In this FIG. 7 example, a first electrical signal B1 from the signal generator 30 is applied before the start of each time that the alternating electric field is being applied in direction F1, and a second electrical signal B2 from the signal generator 30 is applied before the start of each time that the alternating electric field is being applied in direction F2. The first electrical signal B1 will reduce the subject's sensation of the alternating electric field that is about to be applied in direction F1, and the second electrical signal B2 will reduce the subject's sensation of the alternating electric field that is about to be applied in direction F2. Notably, in this example, the electrical signals B1 precede the alternating electric field in direction F1, and the electrical signals B2 precede the alternating electric field in direction F2.

Figure 8:
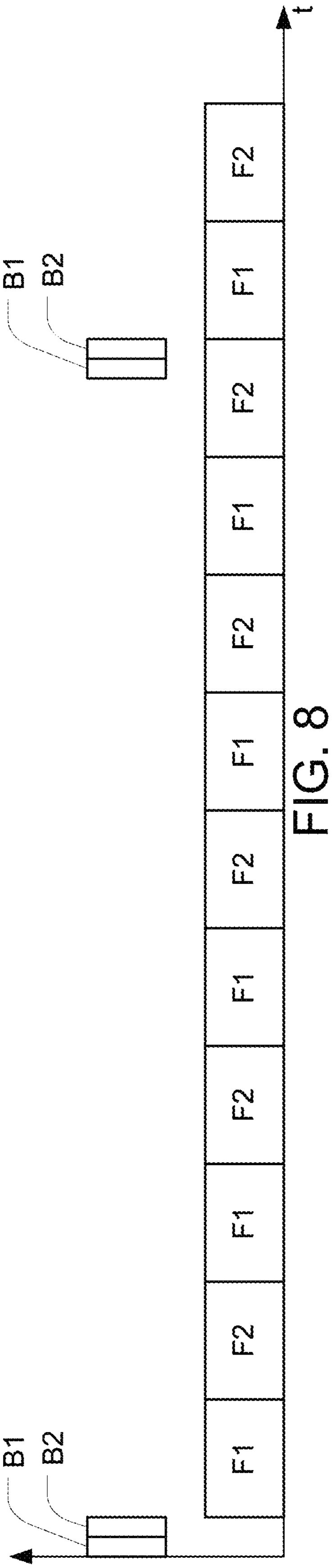
FIG. 8 depicts another example of a suitable timing relationship between the electrical signals and the alternating electric fields.

FIG. 8 depicts another example of a suitable timing relationship between the electrical signals (which reduce the subject's sensation, e.g., as described above in section I) and the alternating electric fields. As explained above in connection with FIGS. 3 and 4, the orientation of the alternating electric field repeatedly alternates back and forth between direction F1 and direction F2. The inventors have recognized that when the electrical signals are sufficiently large, the electrosensation blocking effect of the electrical signals can endure for a significant duration of time (e.g., at least 15 s, at least 30 s, at least 1 min., at least 5 min., or up to 10 min.) after the electrical signals are turned off. Accordingly, the first and second electrical signals may be applied intermittently, with gaps in time that are, for example, at least 15 seconds in duration interposed between successive occurrences. In the FIG. 8 example, the first and second electrical signals B1, B2 from the signal generator 30 are applied during an initial period of time, after which the alternating electric field switches back and forth between directions F1 and F2. The first electrical signal B1 will reduce the subject's sensation of the alternating electric field that is being applied in direction F1, and the second electrical signal B2 will reduce the subject's sensation of the alternating electric field that is being applied in direction F2. Before the long-term effect of the electrical signals wears off (e.g., at 15 seconds), the first and second electrical signals B1, B2 from the signal generator 30 are re-applied. In this example, the electrical signals B1 and B2 are usually applied simultaneously with the alternating electric field.

Note that the intervals of time depicted in FIGS. 5-9 are not drawn to scale. For example, although the B1 and B2 intervals appear to be shorter than the F1 and F2 intervals in FIG. 8, the B1/B2 intervals could in fact have longer durations (or the same duration) as the F1/F2 intervals.

Figure 9:
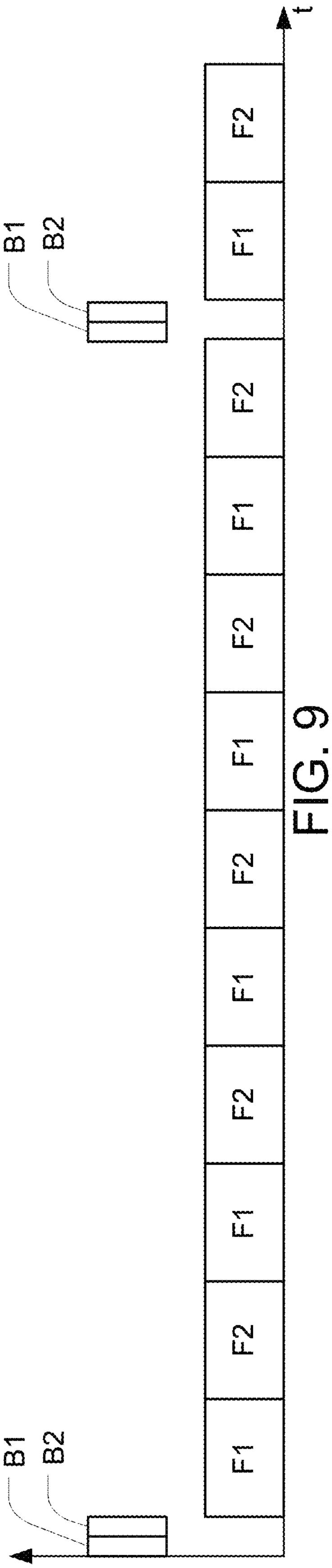
FIG. 9 depicts example of a suitable timing relationship between the electrical signals and the alternating electric fields.

FIG. 9 depicts another example of a suitable timing relationship between the electrical signals (which reduce the subject's sensation, e.g., as described above in section I) and the alternating electric fields. This example is similar to the FIG. 8 example, except that the alternating electric field is switched off whenever the first and second electrical signals B1, B2 are applied.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating a target region of a subject's body with an alternating electric field, the method comprising:

applying an alternating electric field to the target region during a course of treatment, wherein the alternating electric field has a frequency between 50 kHz and 500 kHz; and applying an electrical signal to the subject's body during each of a plurality of time intervals during the course of the treatment, wherein the electrical signal is configured to ameliorate a sensation experienced by the subject that is caused by the applying of the alternating electric field.

2. The method of claim 1, wherein the alternating electric field has field lines that run through the subject's body between a first electrode element and a second electrode element, and wherein the electrical signal travels through the subject's body in a direction that is substantially perpendicular to the field lines.

3. The method of claim 1, wherein the alternating electric field is applied by imposing an AC voltage between a first electrode element configured for positioning on or in the subject's body and a second electrode element configured for positioning on or in the subject's body, the first electrode element having a front face, wherein the electrical signal is applied between a third electrode element configured for positioning on or in the subject's body and a fourth electrode element configured for positioning on or in the subject's body, wherein the third electrode element has a front face having a centroid, and wherein the fourth electrode element has a front face having a centroid, and wherein a line between the centroid of the front face of the third electrode element and the centroid of the front face of the fourth electrode element is substantially parallel to the front face of the first electrode element.

4. The method of claim 1, wherein an orientation of the alternating electric field repeatedly alternates between at least two different directions during the course of treatment, wherein the electrical signal is applied to a plurality of different areas of the subject's body during the course of the treatment, and wherein the application of the electrical signal to the different areas of the subject's body is synchronized with the alternation between the at least two different directions.

5. The method of claim 1, wherein the electrical signal during each of the plurality of time intervals increases an action potential threshold of nerve fibers.

6. The method of claim 1, wherein the electrical signal during each of the plurality of time intervals blocks a propagation of an action potential of nerve fibers.

7. An apparatus for treating a target region of a subject's body with an alternating electric field, the apparatus comprising:

an AC voltage generator having a first AC output that operates at a frequency between 50-500 kHz; and a signal generator configured to generate a first electrical signal during each of a plurality of first times during a course of treatment, wherein the first electrical signal is configured to ameliorate a sensation experienced by the subject that is caused by applying a first alternating electric field to the subject's body.

8. The apparatus of claim 7, wherein the first electrical signal is configured to increase an action potential threshold of nerve fibers in the subject's body or to block propagation of an action potential of nerve fibers in the subject's body.

9. The apparatus of claim 7, further comprising:

a first electrode element configured for positioning on or in the subject's body and a second electrode element configured for positioning on or in the subject's body, wherein the first AC output is applied between the first electrode element and the second electrode element; and a third electrode element configured for positioning on or in the subject's body and a fourth electrode element configured for positioning on or in the subject's body, wherein the first electrical signal is applied between the third electrode element and the fourth electrode element.

10. The apparatus of claim 9, wherein the third electrode element is adjacent to and distinct from the first electrode element, and wherein the fourth electrode element is adjacent to and distinct from the first electrode element.

11. The apparatus of claim 9, wherein the first electrode element and the second electrode element are capacitively-coupled electrode elements, and wherein the third electrode element and the fourth electrode element are conductive electrode elements.

12. The apparatus of claim 9, wherein the first electrode element and the second electrode element are capacitively-coupled electrode elements, and wherein the third electrode element and the fourth electrode element are conductive electrode elements made using a platinum-iridium alloy.

13. The apparatus of claim 9, wherein a single electrode element serves as both the first electrode element and the third electrode element.

14. The apparatus of claim 7, wherein the AC voltage generator has a second AC output that operates at a frequency between 50-500 kHz, and wherein the AC voltage generator is configured to repeatedly alternate between (a) activating the first AC output and (b) activating the second AC output, and wherein the signal generator is further configured to generate a second electrical signal during each of a plurality of second times during the course of the treatment, wherein the second electrical signal is configured to ameliorate a sensation experienced by the subject that is caused by applying a second alternating electric field to the subject's body.

15. The apparatus of claim 14, further comprising:

a first electrode element configured for positioning on or in the subject's body and a second electrode element configured for positioning on or in the subject's body, wherein the first AC output is applied between the first electrode element and the second electrode element;

a third electrode element configured for positioning on or in the subject's body and a fourth electrode element configured for positioning on or in the subject's body, wherein the first electrical signal is applied between the third electrode element and the fourth electrode element;

a fifth electrode element configured for positioning on or in the subject's body and a sixth electrode element configured for positioning on or in the subject's body, wherein the second AC output is applied between the fifth electrode element and the sixth electrode element; and a seventh electrode element configured for positioning on or in the subject's body and an eighth electrode element configured for positioning on or in the subject's body, wherein the second electrical signal is applied between the seventh electrode element and the eighth electrode element.

16. The apparatus of claim 15, wherein the third electrode element is adjacent to and distinct from the first electrode element, wherein the fourth electrode element is adjacent to and distinct from the first electrode element, wherein the seventh electrode element is adjacent to and distinct from the fifth electrode element, and wherein the eighth electrode element is adjacent to and distinct from the fifth electrode element.

17. The apparatus of claim 15, wherein the first electrode element, the second electrode element, the fifth electrode element, and the sixth electrode element are capacitively-coupled electrode elements, and wherein the third electrode element, the fourth electrode element, the seventh electrode element, and the eighth electrode element are conductive electrode elements.

18. The apparatus of claim 15, wherein a single electrode element serves as both the first electrode element and the third electrode element, and wherein another single electrode element serves as both the fifth electrode element and the seventh electrode element.

* * * * *